United States Patent [19]

Klasson et al.

[11] Patent Number: 4,923,474
[45] Date of Patent: May 8, 1990

[54] SLEEVE-SHAPED ARTICLE, PARTICULARLY FOR AMPUTATION STUMPS

[75] Inventors: Bo Klasson, Skärholmen, Sweden; Ossur Kristinsson, Reykjavik, Iceland

[73] Assignee: Ossur Hf, Iceland

[21] Appl. No.: 294,062

[22] PCT Filed: Jun. 25, 1987

[86] PCT No.: PCT/SE87/00299
§ 371 Date: Dec. 27, 1988
§ 102(e) Date: Dec. 27, 1988

[87] PCT Pub. No.: WO88/00032
PCT Pub. Date: Jan. 14, 1988

[30] Foreign Application Priority Data

Jun. 26, 1986 [SE] Sweden ............... 8602855

[51] Int. Cl.$^5$ .......................... A61F 2/78; A61F 2/80; A61F 13/00
[52] U.S. Cl. ...................... 623/33; 623/35; 623/57; 128/157; 128/165
[58] Field of Search ............ 623/33–37, 623/27, 57; 128/157, 165

[56] References Cited

U.S. PATENT DOCUMENTS

| | | | |
|---|---|---|---|
| 980,457 | 1/1911 | Toles | 623/37 |
| 3,377,416 | 4/1968 | Kandel | 623/36 X |
| 3,991,424 | 11/1976 | Prahl | 623/36 |
| 4,634,446 | 1/1987 | Kristinsson | 623/33 |

FOREIGN PATENT DOCUMENTS

| | | | |
|---|---|---|---|
| 2712342 | 9/1977 | Fed. Rep. of Germany | 623/35 |
| 2345138 | 1/1977 | France | 623/34 |
| NO-C-7080 | 8/1898 | Norway | 623/37 |

Primary Examiner—Ronald L. Frinks
Attorney, Agent, or Firm—Bacon & Thomas

[57] ABSTRACT

A sleeve member (1) for enclosing and being fixed to a body part, such as an amputation stump, has a substantially frusto-conical shape with the truncated end thereof completely closed and at least slightly rounded and is made of an airtight material. The sleeve member (1) is characterized in that it substantially is made of an elastic material, at least the distal portion thereof exhibiting such anisotropy with regard to the elasticity that it has a relatively high elasticity in a radial direction and is substantially inelastic axially.

7 Claims, 2 Drawing Sheets

SLEEVE-SHAPED ARTICLE, PARTICULARLY FOR AMPUTATION STUMPS

The present invention relates to a sleeve member for enclosing and being fixed to a deformed part of the body, such as an amputation stump. The new sleeve member is primarily intended as an aid for the application of a prosthesis and stump treatment but may also be used for other purposes, such as the attachment of various auxiliary and training equipment to an amputation stump.

In conventional application of a prosthesis to, for example, an amputation extremity, the stump in question is embedded in a prosthetic sleeve attached to the prosthesis, which sleeve mediates the flux of forces between the amputated body part and the actual prosthesis. Usually such a prosthetic sleeve is produced by making a cast of the amputation stump by means of plaster bandages to obtain a so-called negative of the the stump shape. This negative is then filled with plaster, whereby a plaster copy corresponding to the stump at the time of the casting is obtained. On this negative a sleeve is then formed, usually from a plastic laminate, which sleeve is provided with a closable opening in the extreme or distal end portion thereof. To introduce the stump into the prosthetic sleeve the former is provided with a stocking of knitted fabric, the end of which is then passed through said opening in the bottom of the sleeve, whereupon the soft parts of the stump are drawn downwards into the sleeve by means of the stocking. The knitted stocking is then drawn off the stump and the opening is closed by a valve. Due to the adhesion of the stump skin to the inside of the prosthetic sleeve and the negative pressure which is created in the space between the stump end and the sleeve bottom and maintained by the valve, the prosthesis will be well fixed to the amputation stump in question.

Such a conventional prosthetic sleeve, which for its attachment or suspension is dependent on such an adhesion to the skin and negative pressure, is substantially rigid and has a constant shape, a constant volume and a constant area. Changes of the living stump in any of these parameters thus result in an impaired fitting between stump and sleeve. The suspension is, of course, particularly effected if the volume or circumference of the stump is reduced, such that air may enter via the inner or proximal end, causing a risk that the sleeve will no longer adhere to the stump and that the prosthesis consequently may come off the patient. Any change of the fitting will also give reduced comfort to the patient.

To overcome these inconveniences so-called flexible prosthetic sleeves have been designed. These sleeves are characterized in that they, as the above mentioned rigid sleeves, have a constant area, whereas the shape and volume thereof are variable, resulting, however, in that the circumference of any section is constant. To the extent allowed by the constant circumference these sleeves may, however, conform to the shape and volume changes of the stump, thereby providing a considerably better comfort than the rigid sleeves. The suspension of the prosthesis is as before dependent on adhesion and negative pressure, but due to the properties of the flexible sleeve the risk of admission of air is reduced and the suspension will be safer. Because of the constant area of the flexible prosthetic sleeve it does not, however, always conform to the shape and volume changes of the stump but causes some sliding between the stump skin and the inner wall of the sleeve. While sliding between skin and sleeve is more pronounced for rigid sleeves when external shear forces are transmitted to the stump, it is still a problem when using flexible sleeves and may, for example, give an unpleasant feeling in case of a sore stump skin.

In addition to the fact that the application of the conventional prosthetic sleeves is relatively complicated and thus requires the use of a knitted fabric stocking to accomplish downward drawing of the soft parts of the stump and valve means to maintain a negative pressure, a certain sliding may also be obtained between the prosthetic sleeve and the stump skin, which, on one hand, may cause an impaired suspension and, on the other hand, may lead to discomfort to the patient.

Another problem in connection with amputation stumps is the treatment after the amputation up to the possible application of a prosthesis. When amputating an extremity, for example, it is aimed at providing the amputation stump with properties which to the utmost possible extent will maintain the function of the body part and facilitate the application of a prosthesis. The surgical operation is therefore performed in such a way that an amputation stump that is as firm and insensitive as possible will be obtained. Also the treatment after the amputation is of great importance. A usual post-surgical routine is thus to daily apply elastic bandages around the swollen amputation stump in order to counteract the swelling and accelerate the unavoidable muscle atrophy. When it later on is time for the application of a prosthesis, the prosthetic sleeve should eventually take over the function of the stump bandage. Stump bandaging is thus the most common way of shaping and compressing an amputation stump. Although the stump bandaging is a per se simple procedure, it often happens, however, that it is incorrectly performed which at worst may result in the opposite effect to that intended being obtained. Thus, it is considered to be of great importance that the highest pressure is applied over the distal part and end of the stump. The bandaging of a stump is therefore usually started by applying the elastic bandage axially over the stump end, and then fixing the axial layers by circular winding. The bandaging is ended above the nearest joint to prevent the bandage from sliding on the amputation stump. Since the friction between the skin and the elastic bandage is not considerably great, there is a great risk of sliding of the bandage, which would result in the desired compression effect on the stump end being reduced while the compression of the circular winding would remain. This could result in the blood flow being obstructed and a so-called stasis condition arising. The stump end, which lacks the necessary compression, would then swell even more. This is a well-known problem, and the resulting pear-like stump is technically difficult to provide with a prosthesis. It is also to be noted that most leg amputated persons are old people who often have difficulty in taking care of the stump bandaging themselves in an acceptable manner.

The present invention aims at providing an embedment sleeve which, in addition to having other advantages, eliminates the above mentioned problems in prosthesis application as well as in the post-surgical treatment of amputation stumps. Such an embedment sleeve has the features stated in the subsequent claims and will be described in more detail below.

According to the invention an embedment sleeve it thus proposed which has an essentially frusto-conical shape, the truncated or distal end of which is completely closed and at least slightly rounded, and which is made of an airtight material. The sleeve is characterized in that it substantially is made of elastic material, at least the distal portion thereof exhibiting such anisotropy with regard to the elasticity that it has a high elasticity in the radial direction and is substantially inelastic in the axial direction. Preferably, the anisotropic part of the sleeve extends over at least a major part of the distal half thereof, e.g., at least about one third of the sleeve length, and preferably over at least about half the sleeve length, counted from the distal end.

Due to the elasticity of the embedment sleeve not only the shape and volume thereof but consequently also the area thereof will be variable. Thereby external shear forces transmitted to the sleeve via, e.g., an applied prosthesis will be distributed over the enclosed skin surface substantially independently of the deformation of the body part, such that the contact between each point on the sleeve and the corresponding point on the enclosed skin surface will be maintained without any sliding having to take place between the body part and the sleeve. An adhesive sleeve is thus obtained which requires no opening and closing of the distal end thereof to obtain total contact between the amputation stump and the sleeve. Due to the anisotropy with regard to the elasticity also a more even distribution of external load forces to the soft parts of the stump will be obtained, as will be discussed below.

The advantageous anisotropy properties according to the invention may be obtained by controlling the material composition of the sleeve in various ways and by per se well-known methods in the art. For example, a highly elastic material may be laminated with a layer of another, inelastic material, e.g., rigid wires, which block the elasticity in the axial direction of the sleeve member without affecting the elasticity in radial direction to any considerable extent. Current development seems to indicate that it will also be possible to produce materials, wherein the desired anisotropy may be generated in the material per se.

An embedment sleeve for use with an applied prosthesis according to the invention may thus be supported by the amputation stump as a "second skin" within the outer prosthetic sleeve attached to the prosthesis, suitable means for the connection to the prosthetic sleeve being provided at the distal end of the embedment sleeve. External forces which via the prosthetic sleeve are transmitted to the amputation stump in the form of shear forces and which in a conventional prosthetic sleeve would lead to a motion relative to the stump, will then transfer this motion to the layer located between the outside of the sleeve and the prosthetic sleeve. Sliding between the sleeve and the stump skin will thus not have to occur, and also the most sensitive stump skin will therefore be efficiently protected against chafes and other irritation.

By virtue of the fact that the sleeve, due to the above mentioned anisotropy with regard to the elasticity, is inelastic in the axial direction thereof, a relative even distribution of the suspension force to the soft parts will also be obtained. If the sleeve were completely elastic also in the axial direction, the suspension force would instead substantially be transmitted to the most distal soft parts of the stump or at least give rise to the greatest deformations therein. By the resulting distribution of the suspension force a more efficient suspension will thus be obtained, i.e. lesser occurrence of an undesired "piston motion" of the stump in the prosthesis.

For the coupling to a prosthetic sleeve the above mentioned coupling means in the distal part of the sleeve may, e.g., consist of a central projection formed at the sleeve end and arranged for cooperation with suitable means provided in or applicable to the prosthetic sleeve. Such coupling provides an extraordinarily safe attachment of the embedment sleeve to the prosthetic system while the embedment sleeve on its part, due to its elastic properties, will be well fixed to the stump in question and conform to any deformation of the stump without any tendency to slide. The result is consequently extraordinarily simple and safe application of the prosthesis and very good comfort to the patient when using the prosthesis.

To facilitate the insertion of the elastic stump embedment into an outer prosthetic sleeve the embedment sleeve is suitably provided with an outer layer having a low friction to the outer sleeve. Optionally, the outer sleeve of the prosthesis may be reduced to, or replaced by, suitable support means, such that the embedment sleeve according to the invention at the same time will form the proper prosthetic sleeve.

According to a preferred emodiment the elastic embedment sleeve according to the invention is capable of being at least partially turned inside out. By this is meant that the sleeve should be capable of being turned inside out to then be unrolled onto the stump to which it is to be applied. By such turning inside out stretchings of the sleeve inner wall will result which when unrolling the sleeve onto the stump starting at the distal end thereof, will aid in driving the soft parts of the stump, towards the distal parts of the stump and sleeve and give the soft parts a prestressing in the axial direction. In addition to such prestressing being desirable to i.a. facilitate the blood circulation through the stump at the varying loads occurring, for example, when walking with a leg prosthesis, the effect may be used to replace the previously described stump bandaging and eliminate the problems associated therewith, as will be described further below.

The above described effect may be enhanced in various ways. In a preferred embodiment the embedment sleeve has a material thickness which increases towards the distal end thereof. Depending on how the anisotropy properties of the distal part of the sleeve have been obtained the effect may be further enhanced. Thus, if the anisotropy properties completely or partially have been obtained by means of a substantially axially inelastic lamination on the outside of the sleeve, the so-called neutral line of the curvature when the sleeve is turned inside out is shifted towards the outside of the sleeve, whereby the stretching amplitude is increased.

As indicated above the embedment sleeve according to the invention may thus replace the conventional stump bandaging, since the desired compression on the stump end will be ensured as long as the stump volume is within the limits of the elastic properties of the sleeve. Thus, in principal the same embedment sleeve as is later to be used if a prosthesis is applied, could directly be used for the post-surgical treatment. To this end the above mentioned means at the sleeve end for coupling with the prosthetic outer sleeve may be used to connect any suitable device for actuation of the stump with an axial tensile force. Such an aid, could, for example, consist of a tensile means, for example a spring, attached to an external support, which tensile means will draw the soft parts of the stump in an axial direction, which, on one hand, favours the stump formation and, on the other hand, may relieve the regions of the stump around distal skeleton ends.

By replacing the stump bandage with the stump embedment sleeve according to the invention the desired compression effects of a properly applied stump bandage will thus be obtained, the embedment sleeve also being much easier to apply than the stump bandage without any risk of the occurrence of stasis conditions and swollen stump ends. Additionally, the possibility of static or dynamic loading of the stump in the axial direction is thus offered.

The embedment sleeve according to the invention thus permits a controlled elasticity distributed over the whole sleeve. Thereby, in addition to the above mentioned downward drawing effect of the soft parts of the stump when the sleeve is unrolled, it is obtained that the sleeve will follow the skin movements and distribute external forces. Another advantage of said elasticity is that the sleeve need not be adapted to an individual amputation stump. It will therefore be possible to stock-keep prosthetic sleeves for most of the existing amputation stumps by using a limited number of prefabricated sleeves.

The material of the sleeve may be selected from various plastic and/or rubber materials which meet the necessary elasticity and adhesion requirements. As mentioned above, e.g., laminates may be used. As an example of a suitable elastic base material silicone may be mentioned, which has been found to have properties very well suited for the purpose. The extraordinarily high adhesion which may be achieved between a silicon sleeve according to the invention and the skin of an amputation stump eliminates any tendency to sliding between sleeve and stump.

As mentioned previously the coupling means at the distal end of the sleeve may also be used to connect appliances of another kind than for stump training, stump formation and prosthesis application. An example of such other appliance is training equipment on amputated arm stumps for various normal activities of the daily life, such as eating, cooking, writing, dressing, attending, to one's hygiene, etc.

US-A-980,457 discloses a sleeve member consisting of a sack of an elastic material and an external inelastic sheath. In the illustrated embodiment the lower part of the sheath is corrugated. This permits a certain, very limited expansion of the elastic sack in the radial direction. By means of an adjusting device the sack may, however, due to the corrugated sheath, also be made to expand axially for downward drawing thereof, such that it clearly connects to amputation stump. This sleeve member is thus completely differing from the sleeve member of the present invention which, as described above, has a high elasticity in the radial direction while being substantially inelastic in the axial direction.

The invention will now be further described with regard to some particular, non-limiting embodiments with reference to the accompanying drawings, in which.

Figure 1:
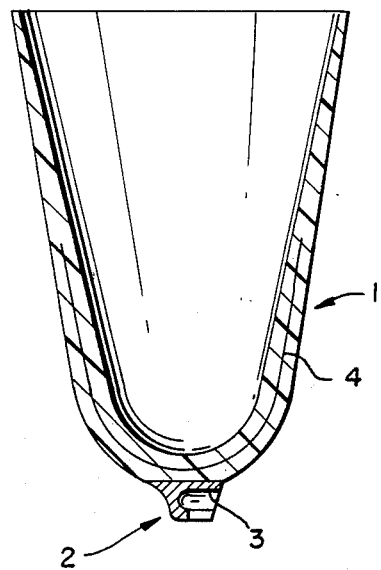
FIG. 1 is a schematic cross-sectional view of an embodiment of an embedment sleeve according to the invention.

The embedment sleeve according to the invention shown in FIG. 1 consists of a substantially frusto-conical sleeve 1 having a closed bottom portion and made of a relatively highly elastic material. e.g. silicone (silicone is a term for so-called silicon plastics or polysiloxanes). The sleeve 1 is adapted to be applied to, for example, the stump of an amputated arm or leg (not shown). In the bottom portion, or distal end, of the sleeve a coupling means 2 is provided for permitting coupling of the sleeve with primarily a prosthesis, but it may, if desired, also be used for connection to a stump treatment device, training equipment or the like. The coupling means 2 is, in the illustrated case, designed as a central downwards extending projection of a rigid material which is provided with a recess 3 partially open to one side and downwards to permit the receipt and fixation of a corresponding locking ball member, as will be described in more detail in connection with FIGS. 4A, B below. The sleeve member 1 has, as illustrated, an increasing material thickness from the proximal end to the distal end thereof, and further, the material composition of at least the major part of the distal sleeve half is anisotropic with regard to the elasticity, so that the sleeve is highly elastic in the radial direction and substantially inelastic in the axial direction. This may, for example, be achieved by means of a suitable axial inelastic reinforcement, in FIG. 1 indicated by the reference designation 4, which may be applied in per se known manner during the manufacture of the sleeve 1 by means of technique known in the art.

Figure 2:
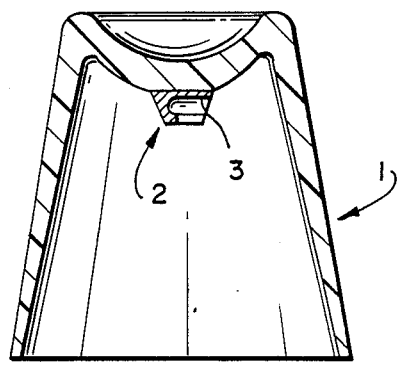
FIG. 2 is a corresponding view as FIG. 1 showing the sleeve after having been turned inside out.

To apply the sleeve illustrated in FIG. 1 to the amputation stump in question the sleeve is turned inside out to the state shown in FIG. 2. From FIG. 3 it can be seen that when turning the sleeve inside out the inside 5 of the curved sleeve portion is subjected to a stretching T, while the outside 6 of the sleeve is subjected to a compression K. When the sleeve 1 is unrolled onto the amputation stump, here indicated by the reference numeral 7, the stretching will revert in the adjacent portion of the sleeve adhering to the skin 8, the skin thereby being drawn downwards into the sleeve in the direction of the arrow 9. As the sleeve is unrolled on the stump, the stretched/curved sleeve portion is successively displaced upwards while the soft parts of the stump are correspondingly successively drawn downwards into the sleeve. The sleeve shown in FIG. 1 has, as mentioned above, the distally increasing material thickness, which provides the greatest downward drawing effect in the distal part of the sleeve, while a higher elasticity and thereby a better adhesion and accomodation of the upper parts of the sleeve is obtained at the same time.

Figure 3:
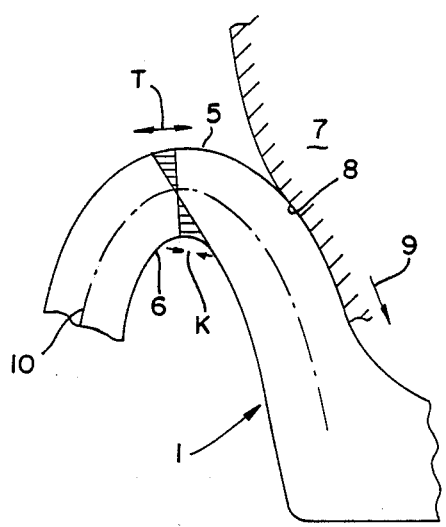
FIG. 3 is a schematic view illustrating the stretching and influence of forces when unrolling an embedment sleeve according to the invention which has been turned inside out.

To increase the downward drawing effect, i.e. move the neutral line 10 indicated in FIG. 3 towards the outside 6 of the sleeve and thereby increase the stretching amplitude, the reinforcement 4 and/or other inelastic reinforcement may, if desired, completely or partially be applied to the outside of the sleeve, which will prevent longitudinal stretching and thereby displace the neutral line 10 towards the outside. As previously mentioned such an outer reinforcement layer may be made friction reducing for the sleeve to be more easily inserted into a prosthetic sleeve or the like.

When the embedment sleeve 1 is applied to the amputation stump it will, due to its elasticity, adhere well to the skin and will conform to any kind of area charge of the stump which may occur upon external loading, such as, e.g., on application of a prosthesis. Since thus substantially any tendency to sliding between the sleeve and the stump is prevented, the sleeve will function as a "second skin", such that external shear forces transmitted via such a sleeve to the stump will transfer any motion or sliding to the layer between the outside of the sleeve and the outer member. Hereby the stump skin will be effeciently protected against chafes and other irritation.

When applying the sleeve 1 in a prosthesis, e.g., as described for FIGS. 4A, B, below, the suspension force will be absorbed in the coupling or connection at the distal end of the sleeve 1. If the sleeve were elastic in its axial direction, the suspension force would be transmitted substantially to the most distal parts of the stump or at least cause the greatest deformations there. Due to the inelastic reinforcement 4 this is, however, prevented, and a more even distribution of the suspension force to the soft parts is obtained. This will in turn result in a more efficient suspension, i.e. lesser occurrence of an undesired "piston motion" of the stump in the prosthesis.

Figures 4A, 4B:
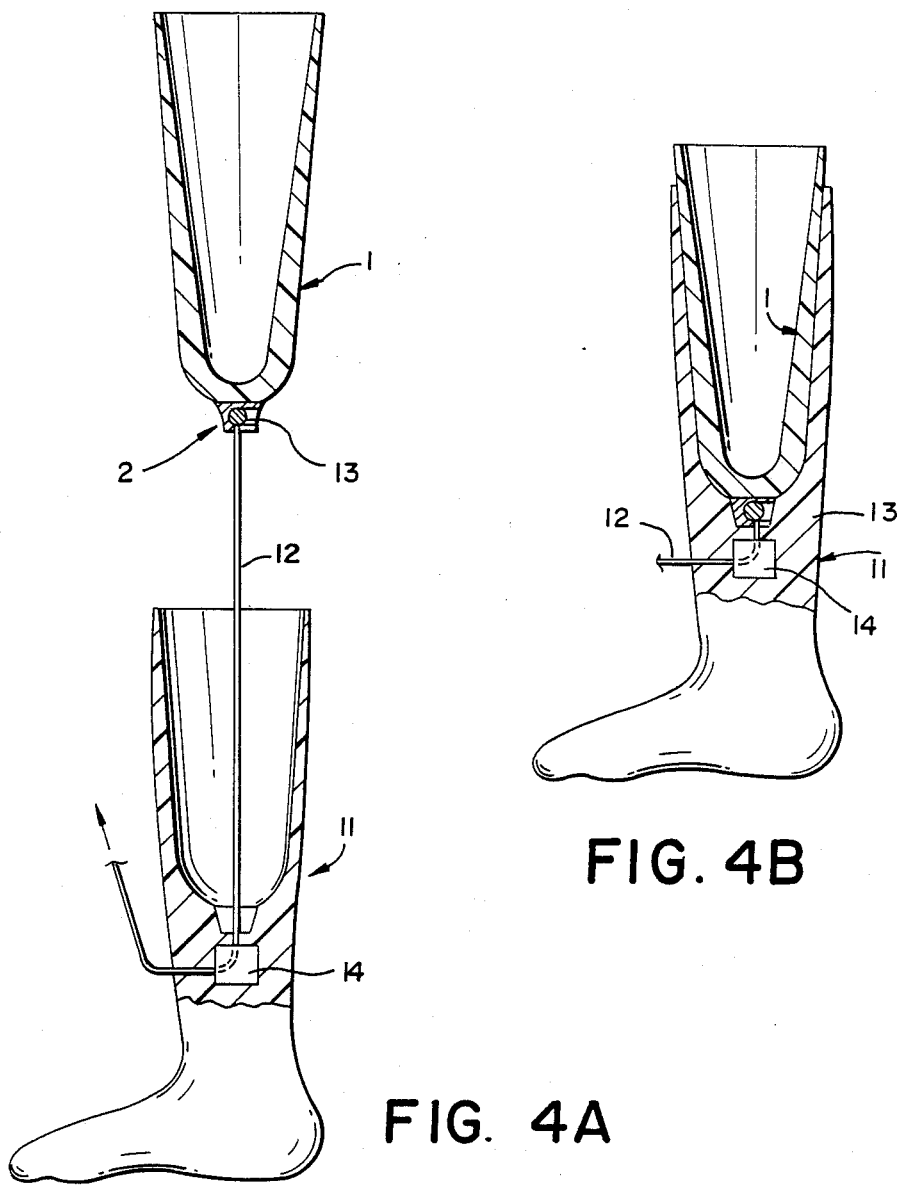
FIGS. 4A and 4B are schematic cross-sectional views of an embedment sleeve according to the invention and a prosthetic system before and after interconnection. respectively.

FIGS. 4A and B schematically illustrate the insertion of an embedment sleeve 1 according to the invention into a prosthetic system 11 in the form of a lower leg prosthesis. The elastic sleeve 1 is unrolled onto the stump, after which the stump with the sleeve in the illustrated case is drawn downwards into the prosthesis 11 by means of a cord 12, which, on one hand, is attached to a ball-shaped coupling member 13 received in the projection 3 on the sleeve of FIG. 1, and, on the other hand, passes through an opening in the prosthesis bottom to a locking means 14. The locking means 14 may be designed in any suitable manner, and may, e.g., in per se known manner be based upon locking by wedge action when the cord 12 is pulled in one direction and release when the cord is pulled in the opposite direction to remove the prosthesis. It is appreciated that such a quick coupling system permits easy removal of the elastic sleeve 1 from the prosthesis for replacement, cleaning or use of the sleeve for stump treatment without the prosthesis, as mentioned above.

With a prosthetic system as above several important advantages in relation to the conventional technique are thus obtained. Thus, the difficult downward drawing of the soft parts by means of a stocking is completely eliminated. The actual taking on and off procedure as a whole is simplified considerably. Owing to the adhesion of the sleeve 1 to the stump and the possibility of motion of the sleeve in relation to the fixing positions of the prosthesis, also sliding against the skin is eliminated. Further, due to the controlled elasticity of the sleeve in the distal part thereof the suspension force will be relatively evenly distributed to the soft parts of the stump.

The invention is, of course, not limited to the particularly illustrated and above described embodiments, but many modifications and variations are obvious to the person skilled in the art and are within the scope of the following claims.

We claim:

1. A sleeve member for enclosing and being fixed to a body part, such as an amputation stump, said sleeve member substantially having a frusto-conical shape, including inner and outer portions, the truncated end of a distal portion of said member being completely closed and at least slightly rounded and said sleeve member being made of an airtight material, characterized in that said sleeve member (1) substantially is made of elastic material, at least the distal portion of said member exhibiting such an anisotropy with regard to the elasticity that it has a relatively high elasticity radially and is substantially inelastic axially.

2. A sleeve member according to claim 1, characterized in that the material thickness increases from a proximal end to the distal end of said sleeve member.

3. A sleeve member according to claim 1, characterized in that the material thickness increases from the proximal end to the distal end thereof.

4. A sleeve member according to claim 1, characterized in that the outer distal end portion of the sleeve member (1) is designed with means (2) permitting coupling to an external device attachable to the sleeve member (1), such as a prosthesis (11).

5. A sleeve member according to claim 1, characterized in that the elastic material which provides said anisotropy with regard to the elasticity comprises at least one layer of a highly elastic material (4) laminated to a layer of another material arranged such that it prevents the elasticity axially without substantially influencing it radially.

6. A sleeve member according to claim 1, characterized in that it is capable of being turned inside out and at least in the distal portion has such a material thickness that the inner portion (5) is stretched when turning the sleeve inside out and when unrolling the sleeve onto the body part (7) gives rise to forces which urge the adhering skin surface (8) towards the distal portion of the sleeve member (1).

7. A sleeve member according to claim 1, characterized in that the outer portion thereof is provided with a friction reducing surface layer.

* * * * *